United States Patent [19]
Yang

[11] Patent Number: 5,167,654
[45] Date of Patent: Dec. 1, 1992

[54] DISPOSABLE URINE AND FECAL WASTE CONTAINMENT PRODUCT

[75] Inventor: Ching-Yun M. Yang, Princeton Junction, N.J.

[73] Assignee: Chicopee, New Brunswick, N.J.

[21] Appl. No.: 464,508

[22] Filed: Jan. 12, 1990

[51] Int. Cl.$^5$ .............................................. A61F 13/15
[52] U.S. Cl. ................ 604/385.2; 604/385.1; 604/367
[58] Field of Search ............... 604/385.1, 385.2, 358, 604/370, 378, 369, 367

[56] References Cited

U.S. PATENT DOCUMENTS

| | | | |
|---|---|---|---|
| 3,875,943 | 9/1973 | Fischer | 604/359 |
| 4,338,938 | 7/1982 | Seavitt | 604/385.2 |
| 4,536,181 | 4/1984 | Cook | 604/387 |
| 4,627,847 | 12/1986 | Puletti et al. | 604/370 |
| 4,681,577 | 7/1987 | Stern et al. | 604/390 |
| 4,685,914 | 8/1987 | Holtman | 604/378 |
| 4,804,380 | 2/1989 | Lassen et al. | 604/378 |

*Primary Examiner*—Randall L. Green
*Assistant Examiner*—R. Clarke

[57] ABSTRACT

A disposable urinary and fecal waste containment product comprising a separate front urinary pad and a separate rear fecal pad detachably joined together is disclosed. Each of the front and rear pads comprise a liquid impermeable backing, an absorbent core and a liquid permeable facing. The rear fecal pad is preferably substantially square or rectangular and has elastic means along its lateral sides and top (waistband) edge to cause it to be gathered and to assume a bowl-like configuration.

5 Claims, 6 Drawing Sheets

DISPOSABLE URINE AND FECAL WASTE CONTAINMENT PRODUCT

BACKGROUND OF THE INVENTION

The present invention relates to a new and improved disposable urine and fecal waste containment product. The product is particularly suitable for use by active adults and provides a means for containing adult discharges of urine and fecal waste. The product has a high liquid impact capacity, high liquid retention, contains fecal waste without leakage and allows the skin of the wearer to remain dry.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent batt is disclosed in U.S. Reissue Pat. No. 26,151.

The wadding type of product was replaced, for the most part, by an improved absorbent batt which comprises what is termed "fluffed wood pulp fibers". This absorbent batt comprises a layer of individualized wood pulp fibers with the layer having substantial thickness. A diaper which incorporates such fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and, hence, produces an improved diaper over diapers using wadding as the absorbent layer.

Although fluffed wood pulp absorbent batts have a good absorptive capacity, the efficiency with which the capacity is used in a diaper or sanitary napkin is poor. The reason for this is that the fluid to be absorbed is generally deposited in a localized area within the absorbent batt, and the ability of the fluid to move along the plane of the batt is poor. The fluid tends to follow a radial wicking path and consequently moves to the closest edge of the batt where it generally is no longer contained and the product leaks.

A number of years ago, "superabsorbent materials", i.e., materials which will absorb many times their weight of liquid, were developed. Since the development of such materials, attempts to incorporate them in absorbent products such as diapers to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

Certain forms of peat moss are highly absorbent materials, and their use in absorbent products has previously been suggested. U.S. Pat. No. 4,170,515 to J-M Lalancette discloses a method for bleaching peat moss, thereby making it suitable for use in absorbent dressings and the like. U.S. Pat. No. 4,226,237 to Y. Levesque discloses a layered absorbent structure including a first layer comprising cellulose fibers and, adjacent to the first layer, a second layer comprising, in admixture, peat moss and finely ground mechanical wood pulp. U.S. Pat. Nos. 4,215,692 and 4,507,122, both issued to Levesque, disclose that peat moss, in combination with mechanical wood pulp, can be formed into a low density board, dried, and then compressed to form a thin, flexible, absorbent board which may be used directly in absorbent products. U.S. Pat. No. 4,473,440 to Ovans discloses a peat moss containing board which is manufactured by first conditioning the board to a specific water content and then densifying the board by calendaring between rollers. U.S. Pat. No. 4,676,871 discloses an air laid peat moss board suitable for use in absorbent products which is made by harvesting and individualizing peat moss, drying the peat moss, entraining the peat moss in a gas stream, and then condensing the entrained peat moss to form a low density board. The disclosures of each of these patents are herein incorporated by reference.

In designing a disposable urine and fecal waste containment product, one must be mindful of the special problems of an incontinent adult. First, the void of an adult generally is much higher in volume than that of an infant, so a device with greater absorptive capacity than that of an infant's diaper is needed. Second, a bulge under clothing is accepted by society for an infant, but the ambulatory adult with an incontinence problem longs for a product which is not visible through ordinary clothing. Third, the proportions and shape of the legs and torso of the adult differ considerably from those of an infant. Therefore, a mere enlargement of an infant diaper is not a satisfactory product.

U.S. Pat. No. 3,525,337 discloses an absorbent element for sanitary napkins or the like consisting of an accordion-pleated pad formed from a thin layer of absorbent fibers faced on each side with sheets of absorbent cellulose wadding. The pleats are secured in their folded configuration by having the peaks of the folds on one side of the pad attached to an anchoring sheet.

U.S. Pat. No. 4,685,914 discloses a disposable urinary pad which utilizes superabsorbent material. The pad disclosed in this patent comprises a liquid-impermeable, substantially flexible shell containing a superstructure consisting essentially of a fibrous web of hydrophobic, wet resilient, dry resilient fibers and an absorbent medium in intimate contact with at least a portion of said superstructure and at least a portion of said shell. In a preferred embodiment, the superstructure is a corrugated fibrous web, e.g., of polyester fibers, and the absorbent medium is a superabsorbent material.

U.S Pat. No. 4,501,586 discloses an absorbent structure comprising a moisture-impermeable backing, an absorbent batt and a moisture-permeable cover covering at least the side opposite the moisture-impermeable backing. The absorbent batt is of loosely-compacted, cellulosic fibers and is provided with a reservoir having a capacity of at least 10 cc. The reservoir is formed by compression of the fibers in the reservoir zone and is located so that the product, when worn, retains the proper shape.

U.S. Pat. No. 4,731,070 discloses an absorbent article particularly suitable for use by male and female incontinents. The absorbent article includes a urine receptacle pocket offset to one end of the product and formed by folding the product and adhering together portions of a moisture impervious sheet that are folded over side marginal edges of an absorbent batt.

U.S. Pat. No. 4,681,577 discloses a disposable urine and fecal waste containment product for adults. The product has a liquid-impermeable, substantially flexible shell containing a front urinary portion and a rear fecal portion. The urinary and fecal portions appear to be separate, but there is no indication that the front and rear portions of the product are detachably connected to one another.

The present invention provides a new and improved absorbent product which possesses a large storage capacity, which is soft and comfortable, which can be designed so as not to be apparent through normal clothing and which utilizes a substantial portion of the absorptive capacity of superabsorbent materials or of highly absorbent peat moss materials. Still further, the product retains fecal waste matter thus keeping it from the clothing of the wearer.

SUMMARY OF THE INVENTION

The present invention relates to a disposable urine and fecal waste containment product comprising a separate front urinary pad and a separate rear fecal pad detachably joined to one another.

The front urinary pad comprises a liquid impermeable backing, an absorbent core and a liquid permeable facing and is capable of absorbing and storing a relatively large quantity of liquid. The liquid impermeable backing may be, for example, a polymeric foam shell into which an absorbent core is placed or a liquid impermeable film such as a polyolefin film. Absorbent materials utilized in the urinary pad include such materials as ground wood pulp, non-cellulosic synthetic fibers, peat moss, superabsorbent materials, and mixtures or combinations thereof. A liquid permeable facing, disposed upwardly in the pad toward the wearer of the product, is generally adhered to the liquid impermeable backing to entrap the absorbent core therebetween. The front urinary portion will generally have a cup-like configuration to best receive and contain liquid.

The rear fecal pad also comprises a liquid-impermeable backing, an absorbent core and a liquid permeable facing. Generally, the liquid-impermeable backing will be a polyolefin film, such as a polyethylene film. Although it is not necessary that the rear fecal pad have the same absorptive qualities as the front urinary pad, it should be capable of absorbing any liquids expelled by the wearer along with fecal matter. The same absorbent materials mentioned above for use in the front urinary pad may be used in the rear fecal pad. The rear fecal pad is substantially square or rectangular in shape and has a top, bottom and two lateral edges. It is detachably joined near its bottom edge to the front urinary portion, as by an adhesive element such as tape or a permanently tacky, pressure sensitive adhesive. The rear fecal pad has elastic means along its lateral edges and its top edge so as to cause the pad to be gathered and to assume a bowl-like configuration. It should substantially cover and conform to the hip area of the wearer.

The product of this invention has a high impact capacity, i.e. the product accepts a relatively large quantity of liquid quickly and retains it. Furthermore, the product does not leak or spill over. In other words, once the urine enters the pad, the urine remains entrapped within the product. The product also has a high liquid-holding capacity. In addition, the product maintains its surface dry thereby keeping any moisture away from the skin of the wearer. Still further, the product of this invention permits air circulation in the region where the product is worn which results in a high degree of comfort. The product will contain absorbed liquid and deposited fecal waste matter even when pressure is placed upon the product during use.

Another advantage of the product of this invention stems from the fact that the urinary and fecal portions of the product are separate and detachably joined. Some incontinence sufferers do not require full time bowel protection. Thus, after a discharge, they could detach the fecal portion of the product and continue to use the urinary portion. Alternately, if the urinary portion became full, it could be discarded and replaced with a new unit without wasting the fecal portion of the product.

DETAILED DESCRIPTION OF THE INVENTION

Figure 1:
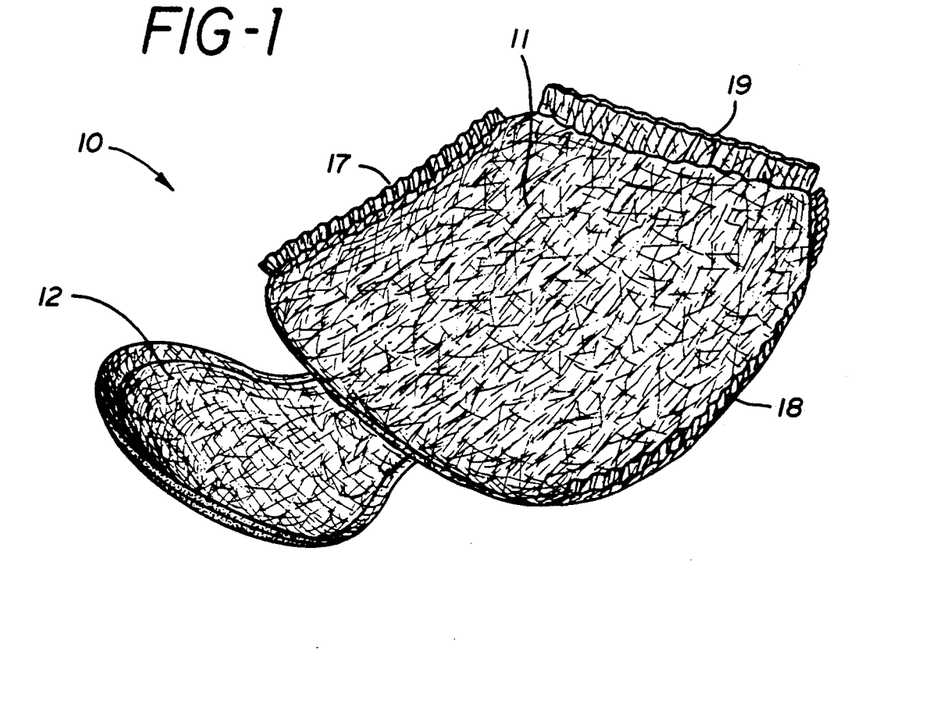
FIG. 1 is a perspective view of a disposable containment device of this invention.

FIG. 1 illustrates an embodiment of a disposable urine and fecal waste containment product 10 of this invention. Rear fecal pad 11 is detachably joined, near its bottom edge, to front urinary pad 12, as by adhesive means. Although the illustrated embodiment shows urinary pad 12 attached at its top surface to the bottom surface of fecal pad 11, it will be appreciated that other arrangements are possible. For example, the urinary pad might be attached at its bottom surface to the top surface of the fecal pad, or the fecal pad may even be provided with a slit or pocket into which a portion of the urinary pad can fit so as to detachably join it thereto. Front urinary pad 12 is generally cup-shaped in configuration and, although a pad with a boat-shaped, foam cup shell is illustrated, other types of pads, as described in more detail below, may be used. Rear fecal pad 11 is substantially square or rectangular in shape and is provided with elastic means 13 and 14 so that it is gathered at its upper and side edges as shown in FIG. 1 and assumes a bowl-like configuration.

Each of the front urinary pad and the rear fecal pad comprise a liquid-impermeable backing, an absorbent core and a liquid-permeable facing, which elements can be described in more detail as follows.

The liquid-impermeable backing for either the front urinary or the rear fecal pads may be a liquid-impermeable polyolefin film, e.g., polyethylene or polyethylene terephthalate. Although the liquid-impermeable backing for the rear fecal pad generally will be a film, a liquid-impermeable, flexible shell, generally a polyethylene-containing foam shell which is preformed by a thermal molding process known in the art, may be used as the liquid-impermeable backing for the front urinary pad. The shell generally has a boat-like shape and ranges in thickness from about 1/64 to ¼ inch, preferably about 1/16 inch, in thickness. The shell generally has a length which ranges from about 4 inches to about 12 inches, a width measured from one rim to another across the top space from about 2 inches to about 7 inches, and a depth, measured from a line extending across the width at the upper shell rim in the central portion to the bottom of the shell interior, from about 0.5 to about 2.5 inches. The shell is resilient, and, when deformed, should substantially return to its original shape.

On the underside of the liquid-impermeable backing of either the front urinary pad or the rear fecal pad, or both, of the containment device, there may be placed adhesive attachment means for temporarily, but securely, adhering the device to the wearer's nether garment. The attachment means may comprise adhesive lines covered with release strips which, when peeled from the adhesive strips, leave the adhesive ready for use. The attachment means might also comprise pressure-sensitive adhesive tape, said tape having a first face permanently adhered to the pad and an opposite second face adapted to be temporarily attached to the undergarment. In lieu of such attachment means, the product could also be provided with a strip of fabric for wrapping around the waist, or could be used in conjunction with a garment to facilitate wearing and use.

The ethylene-containing polymer foam shell can be prepared by known thermal molding processing. One preferred formulation for forming the ethylene-containing polymer foam material is identified as Volara Type A, which is a crosslinked polyethylene foam. The product is manufactured and sold by Voltek, Ind., Lawrence, Mass. The expression "ethylene-containing polymer foam" used herein includes polyethylene homopolymer and ethylene-containing copolymers, preferably containing a major portion, by weight, of ethylene. It is preferred that the polymer present be crosslinked. Preferred comonomers, for preparing the polymers, include vinyl acetate, acrylic and methacrylic acids and esters, such as ethyl acrylate. Blends of such polymers can also be used. Preferably, the formulation is prepared in sheet form at approximately ⅛ inch thickness. The sheet is subjected to thermal molding at a temperature of bout 260° F. to form the foam shell.

The liquid-permeable facing provided on the structures of the present invention is an apertured film, nonwoven fabric or the like having a high degree of moisture permeability. For example, the fabric may be polyester, polyethylene, polypropylene, bicomponent, nylon, rayon, or the like fibers. Preferably, the fabric used for the cover is a lightweight fabric in the range of 0.3 to 5.0 oz. per square yard and with a density less than 0.2 gm/cc. The most suitable fabrics have high loft, softness and drape characteristics. In the preferred embodiment, the cover is a web of through air bonded bicomponent (polyester/polyethylene) fiber. Excellent results have been obtained using such a fabric of 0.5–0.7 oz/yd$^2$ formed from 3 denier 1¼ inch bicomponent staple fiber.

Turning now to a more detailed description of the absorbent components of the pad of this invention, hydrophilic fibers from which the absorbent core may be made include wood pulp fibers. Wood pulp is highly liquid absorbent and wettable, but collapses when wet. Non-cellulosic synthetic fibers such as but not limited to polyolefin fibers (polyethylene, polypropylene, and bicomponent fibers) are resistant to wet collapse. Thus, it has been found that by blending these two materials together, a medium with an optimum absorbency can be obtained. Blending about 5 to 50 weight %, preferably about 20-25 weight %, of non-cellulosic synthetic fibers with the wood pulp fibers leads to a material with markedly improved wet collapse properties compared to 100% wood pulp, but which substantially retains the absorbent and wettability properties of the wood pulp. In one embodiment of this invention, the absorbent core comprises approximately 77% by weight wood pulp and approximately 23% Pulpex ®, the latter being a synthetic polyethylene wood pulp supplied by Hercules, Wilmington, Del., USA.

To further enhance the liquid absorbent qualities of the absorbent core, it may be desirable to include therein certain "superabsorbent" materials. These are generally water-insoluble, water-swellable polymeric substances capable of absorbing water in an amount which is at least 10 times the weight of the substance in its dry form. The superabsorbent is in the form of powders, fibers, spheres, particles, bits of film, globules, or the like.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides including, for example, cellulose and starch and regenerated cellulose which are modified by being carboxylalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula wherein $R^1$ and $R^2$ are selected from the group consisting of hydrogen and alkyl having 1 to 4 carbon atoms, X and y are selected from the group consisting of —OH, —O(alkali metal), and —NH$_2$, wherein m is an integer having a value of 0 to about 5000, n is an integer having a value of 0 to about 5000, m plus n is at least 500, p is an integer having a value of 0 or 1, and q is an integer having a value of 1 to 4.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly (N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably crosslinked, either chemically or by irradiation. Still another more recent type is a derivative of isobutylene-maleic anhydride copolymer.

The absorbent core generally comprises about 10 to 50 weight %, based on its total weight, of superabsorbent. In the preferred embodiment of this invention, the superabsorbent is poly-(sodium acrylate) and the superabsorbent comprises about 33 weight % of the total weight of the composite web. The balance of the composite web is a blend of wood pulp and Pulpex ® in a weight ratio of 77:23.

The absorbent composite web of wood pulp/noncellulosic synthetic fiber/-superabsorbent can be prepared by methods known in the art utilizing a transverse webber as disclosed in U.S. patent application Serial No. 99,875, filed Sep. 22, 1987, the disclosure of which is incorporated herein by reference. A single feed of a combined pulp/synthetic fiber material may be fed to the webber, ground so as to individualize the fibers and then fed into an air stream into which superabsorbent material is also introduced. The combined pulp/synthetic fiber/superabsorbent may be collected thermally bonded together to produce a stable web. Desirably, this web comprises a homogenenous blend of the three materials; however, there may be some settling of superabsorbent particles to the bottom of the web during subsequent processing steps.

In lieu of, or in addition to, the use or superabsorbent materials as described above, it may be desirable to utilize the high absorptive qualities of peat moss products in the products of this invention. Sheets of tenderized peat moss may be made by methods well known in the art, such as those disclosed in the patents the disclosures of which were previously incorporated by reference. Generally, the raw peat moss material utilized is peat moss of the sphagnum variety and is preferably capable of absorbing at least about 15 times, preferably about 20 times, its weight in water. The peat moss is generally screened and then separated into a usable fraction and peat fines. The screened peat moss may be combined with other absorbent materials, preferably fibrous and cellulosic in nature. These art-recognized materials may include Kraft, wood pulp and mechanical wood pulp. As used herein, the term "mechanical wood pulp" is meant to include ground wood pulp, thermomechanical pulp and refiner wood pulp. The common characteristic of these mechanical pulps is that no attempt has been made to separate the fibers by chemical means although they may later, after being reduced to fine particulate matter, be subjected to chemical treatment. Preferably, when mechanical wood pulp is used in the board of this invention, such mechanical wood pulp has a Canadian Standard Freeness (TAPPI TEST METHOD T-227) of from about 60–500 and preferably from about 150–300. Another valuable material used in combination with peat moss is Kraft wood pulp. This material is generally a chemically treated, long fibered pulp such as sulfite and sulfate wood pulps. A suitable mixture of ingredients for the absorbent boards of the invention may comprise from about 5 to about 20 percent by weight of Kraft wood pulp, with the remainder being essentially peat moss. It is understood that these compositions are preferred peat moss embodiments and that those familiar with the art may find a wide range of peat moss compositions as well as other absorbent materials, i.e., superabsorbents, for use with the products of this invention.

The above peat mixtures can be additionally combined with fibrous means comprising polymer fibers, preferably polyester fibers, and most preferably staple-length polyester fibers. The preferred polyester fibers are disposed to maintain the integrity of the product during processing and use, without subtracting from the intended mechanical flexibility. Preferably the polyester material or other suitable fibrous material is slurried with water in a pulper prior to being mixed with the preferred peat moss compositions. The preferred absorbent elements of this invention can comprise about 2.5% to about 20.0% polyester by weight, preferably about 4.0 to 8.0% polyester by weight. The term "peat moss", then, as used herein to describe the first absorbent member of the absorbent core, is intended to include peat moss products comprising, in addition to particles of peat moss, cellulosic fibers and polymer fibers as described above.

The mixture of screened peat moss and selected fibers are processed into an absorbent element by methods known in the art. Generally, the screened peat moss and selected fibers are slurried together to form an aqueous slurry which is preferably flowed onto a Fourdrinier wire and dewatered to form the starting board. In the most preferred embodiment, a laminate is then made from the peat board and layers of Kraft wood pulp. The resulting composite board is then conditioned to contain a prescribed moisture content and calendared.

The absorbent peat moss elements prepared as described above tend not to be flexible enough for use in an absorbent garment without undergoing "tenderizing", i.e., processing by any number of known methods to increase the cross-direction flexibility of the board. See, for example, the disclosure of U.S. Ser. No. 242,274, filed Sep. 12, 1988, which discloses a method of tenderizing the absorbent element by a special cutting process which severs the peat moss portions of the element but which leaves those portions linked with fibrous means to produce a hinge-like effect in the resulting element. Other "tenderizing" methods which might be employed to enhance the flexibility of the absorbent board are microcorrugation and perfembossing as disclosed in U.S. Pat. No. 4,605,402 to Iskra.

One or more layers of peat moss material may be used as the absorbent element. Obviously, the greater the absorptive capacity which is desired for the final absorptive product, the more absorptive capacity must be provided in the absorbent core. As the peat moss boards decrease in flexibility with thickness, it may be desired to utilize two (or more) layers of peat moss board in lieu of one thicker layer.

Figure 2:
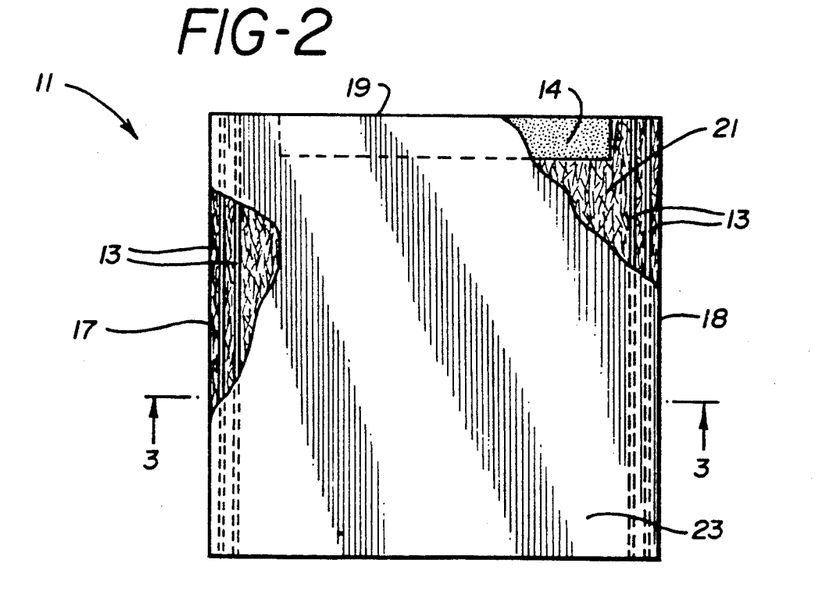
FIG. 2 is a top view of the rear fecal pad of a disposable containment device of this invention prior to activation of the elastic means located at the top and side edges thereof.
Figure 3:
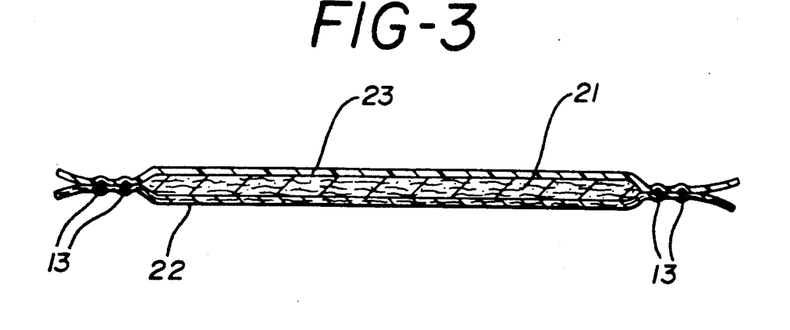
FIG. 3 is a cross-sectional view taken along line 3—3 of FIG. 2.

Turning now to the specific embodiments illustrated in the Figures, FIGS. 2 and 3 illustrate an embodiment of the rear fecal pad 11 prior to contraction of the elastic means. The pad is substantially square or rectangular in shape, with typical dimensions being 10" along the lateral edges and 12" along the top and bottom edges. An absorbent core 21 is sandwiched between a liquid-impermeable backing 22 and a liquid permeable facing 23, and is generally smaller in dimensions than both said backing and said facing. Elastic means 12 along the lateral edges 17,18 of pad 11 and elastic means 14 (not shown in FIG. 3) along the top, edge 19 of the pad, when contracted, cause the pad to assume a bowl-like configuration and substantially conform to the shape of the wearer's buttocks.

The absorbent material used in absorbent core 21 of the rear fecal pad can be any of the absorbent materials, or combinations thereof, previously described. For example, it could comprise wood pulp, wood pulp in combination with synthetic fibers, either of the foregoing in combination with superabsorbent material, or peat moss.

Elastic means 13,13 such as elastic threads are preferably used along the lateral edges of the pad to cause it to gather. The rubber threads, provided in pairs approximately ¼" apart, are applied to the side edges of the backing material and adhered intermittently thereto. The threads are secured to the backing in a stretched condition (e.g., about 50% stretch). When the threads are allowed to contract, gathered portions are formed.

Although the same elastic means may also be used along the top edge 19 of rear fecal pad 11, it is generally preferred to use a heat-shrinkable film or extensible film or foam which is adhered to the pad in a tensioned condition relative thereto. Examples of a suitable heat-shrinkable film include a three-ply coextruded film comprising two outer layers of LLDPE and a center ply of ethylene vinyl acetate (28% vinyl acetate, melt index 6). This film is advantageous in that it can be glued to typical backing and facing materials, and is conveniently thermally activated (shrunk to an elastic state), so as to cause gathers, by the application thereto of hot air. An extensible foam which can be adhered to the pad in a tensioned condition and thereafter released to create the desired gathers includes a polyurethane foam.

Specific embodiments of suitable front urinary portions are disclosed and claimed in copending patent applications Ser. No. 464,270, Ser. No. 464,487, Ser. No. 464,493and Ser. No. 464,490, filed simultaneously herewith, the disclosures of which are herein incorporated by reference. They are also illustrated herein in FIGS. 4–12.

Figure 4:
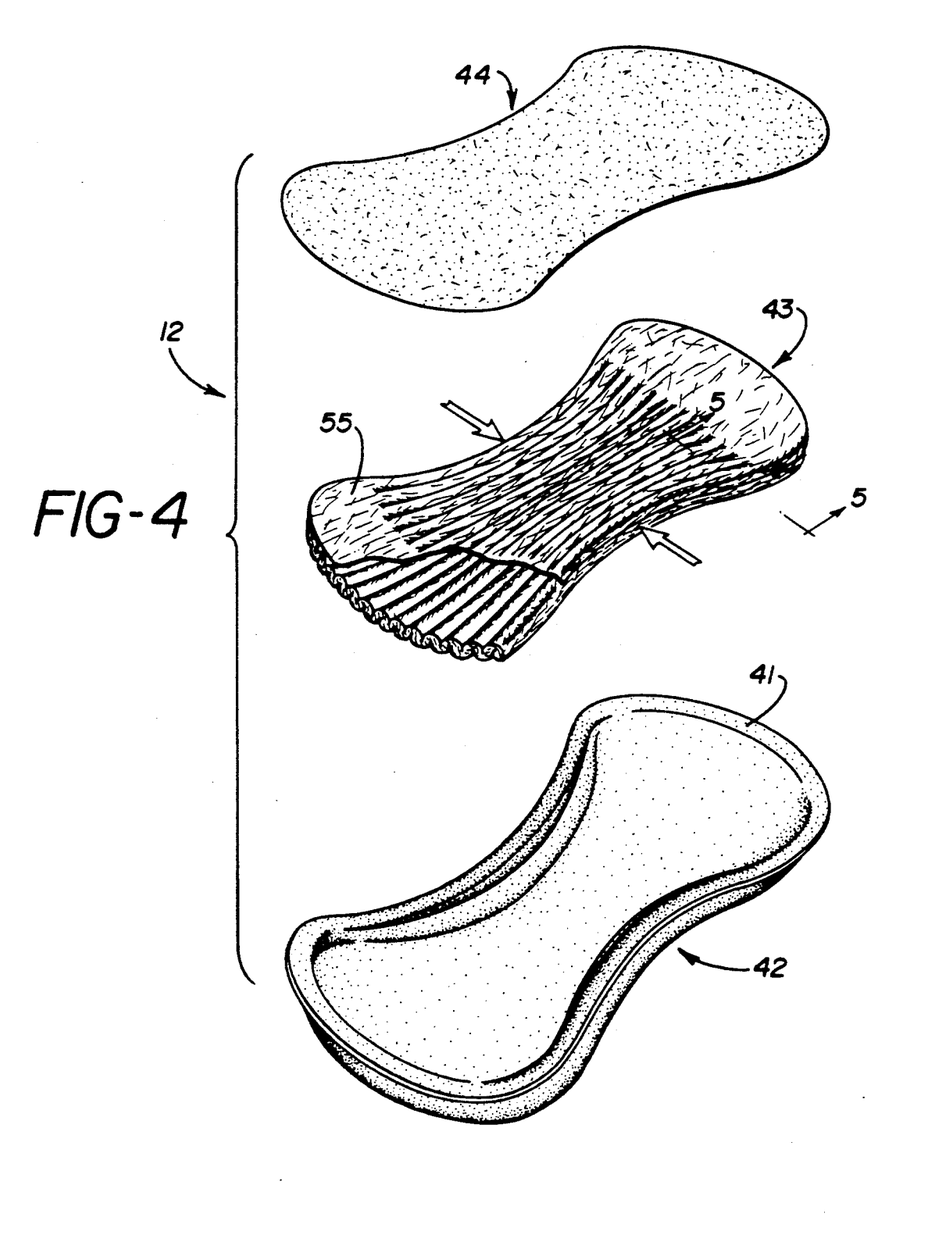
FIG. 4 is an exploded perspective of the structural parts, prior to assembly, of a front urinary pad comprising the disposable containment device of this invention.
Figure 5:
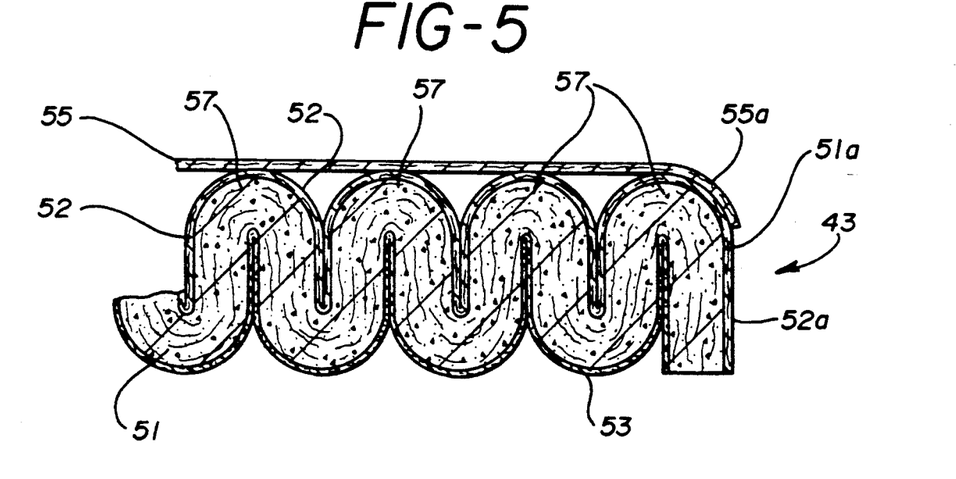
FIG. 5 is a cross-sectional view taken along line 5—5 of FIG. 4.

FIGS. 4 and 5 show one embodiment of a suitable front urinary pad 12. FIG. 4 illustrates the embodiment with the structural elements thereof separated and showing their spatial relationship. The shell 42 is a liquid-impermeable shell which is preformed by a thermal molding process known in the art. Absorbent core 43 is "squeezed" at its center, as illustrated by the directional arrows in FIG. 4, in order to fit it into the shell 42. The facing 44 is a liquid-permeable, generally hydrophobic fibrous web, typically having a basis weight of 0.5 oz/yd$^2$. The three elements, the shell 42, the absorbent core 43, and the facing 44, are combined as shown in the drawing, the facing being sealed at its periphery to the flange 41 of the shell so as to provide a unitary product.

FIG. 5 is a cross-sectional view along line 5—5 of FIG. 4 of a portion of absorbent core 43. The absorbent core 43 comprises an absorbent web 51 of wood pulp fibers, synthetic staple fibers and superabsorbent [preferably poly-(sodium acrylate)]. Absorbent web 51 can be prepared by methods well-known in the art. For example, a single feed of a combined wood pulp/synthetic fiber material may be fed to a webber, ground so as to individualize the fibers and then fed into an air stream into which superabsorbent material is also introduced. The blended pulp/synthetic fiber/superabsorbent materials are collected on a carrier tissue 53 after which they are treated with hot air to produce stabilized web 51. A first liquid-permeable nonwoven fabric 52 comprising a thermally bonded web of bicomponent fibers (polyester core/polyethylene sheath) is then placed on top of the tissue-carried, heat-stabilized web 51. The resulting laminate is then corrugated in known fashion to produce the pleated structure shown in FIG. 5. A second nonwoven fabric 55, identical to nonwoven fabric 52, is secured by heat treatment to the peaks 57 of the folds of the pleated web 51 to thereby stabilize the same and to provide absorbent core 43 as seen in perspective in FIG. 4.

As can be appreciated from FIG. 5, right-hand side, second nonwoven fabric 55 has a width which is greater than the width of pleated web 51 to which it is applied. As a result, the side marginal portions 55a of second nonwoven fabric 55 extend over and are continued at least partially downward over the side edges 51a of corrugated member 51. When absorbent core 43 is inserted into shell 42, side marginal portions 52a of first liquid-permeable nonwoven fabric 52 and side marginal portions 55a of second nonwoven fabric 55 provide means for transferring discharged liquid from the area of impact to the bottom of shell 42. In this manner, a large volume of voided liquid can be held in waste in front urinary pad 12 until it is taken and retained by absorbent core 43.

The structure shown in FIGS. 4 and 5 are disclosed in greater detail in simultaneously filed U.S. patent application Ser. No. 464,270, the teachings of which are incorporated herein by reference.

Figure 6:
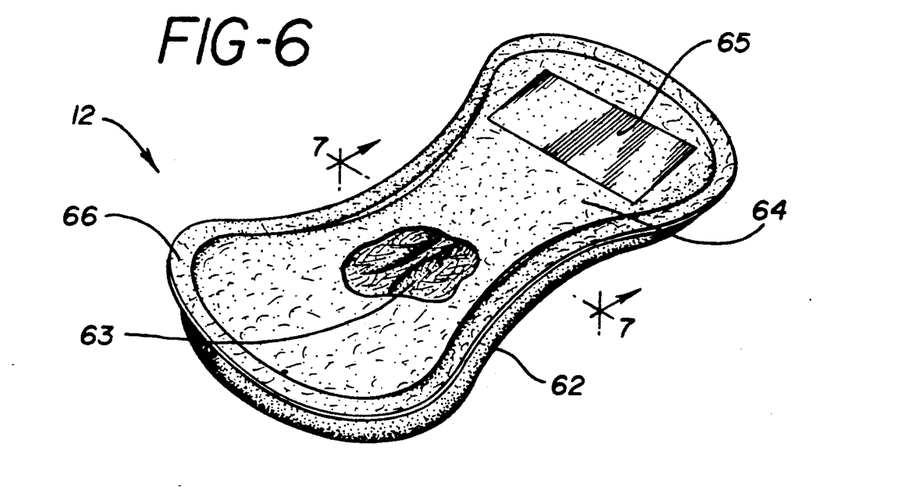
FIG. 6 is a perspective view, with parts cut away, of another embodiment of a front urinary pad comprising the disposable containment device of this invention.
Figure 7:
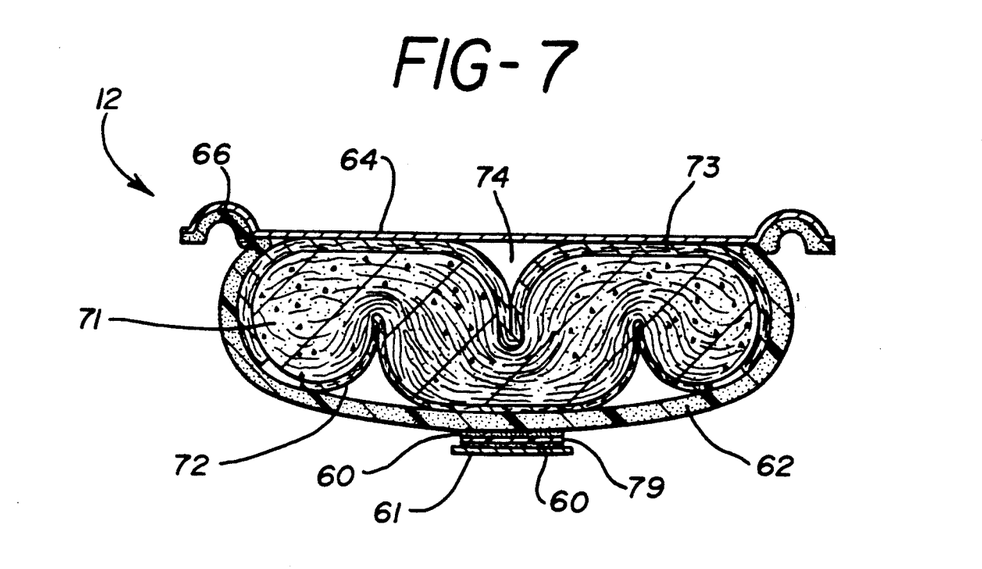
FIG. 7 is a cross-sectional view taken along line 7—7 of FIG. 6.

FIG. 6 is a perspective view of another embodiment of a urinary pad 12 of the containment product of the present invention. The liquid-impermeable backing 62 is again a foam shell which is preformed by a thermal molding process known in the art and referred to earlier herein. Absorbent core 63, pleated in an M-configuration, is fit into shell 62. The facing 64 is again a liquid-permeable, generally hydrophobic fibrous web. The three elements, i.e. shell 62, absorbent core 63 and facing 64, are combined as shown in FIG. 7, the facing being sealed at its periphery to flange 66 of the shell so as to provide a unitary product. Also illustrated in FIG. 6 embodiment is adhesive means 65 for detachably joining the front urinary pad to a rear fecal pad to create the containment product of the invention.

FIG. 7 is a cross-sectional view of pad 12 illustrated in FIG. 6. Absorbent core 63 comprises an absorbent medium 71 and a transfer layer 73. The absorbent medium 71 comprising a blend of wood pulp fibers, synthetic fibers and superabsorbent material deposited onto a layer of tissue 72 is faced on one surface with transfer layer 73, and is then pleated into the M-configuration shown in FIG. 7. The transfer layer 73 is preferably a layer of synthetic fusible fibers and should be a high loft material having high resiliency and substantially no resistance to liquid flow. Resin bonded polyester fabrics have been found to be particularly suitable for use in the transfer layer. A preferred embodiment utilizes a nonwoven fabric which has a basis weight of 1.5 oz/yd$^2$, is resin bonded, and comprises 6 denier, 1½ inch staple polyester fibers. The binder resin is derived from an acrylic emulsion and comprises 25 weight % of the fabric weight. The transfer layer may be a discrete layer of fabric or may be created in-situ by applying fiber and resin to one surface of the absorbent medium.

The M-configured pleat in absorbent core 63 (comprising absorbent medium 71 plus transfer layer 73) can be formed using a three-finger device, the center finger remaining static while the two outside fingers move toward the center stationary finger. This causes the M-fold and a reduction in the width of the pad in its center portion. Generally, core 63 is squeezed at its center and then placed into the liquid-impermeable foam shell which holds it in the pleated configuration. However, the pleats do not have to be restricted to the center portion of the core and could be extended throughout the entire length thereof.

In forming the M-fold, a channel 74 is created in approximately the center of the pad in a lengthwise direction which serve to hold discharge until absorbed by the absorbent core. The transfer layer 73 is configured, after the M-folding step, so as to extend substantially down the side of the pleated absorbent medium 71 to provide a liquid path to the bottom of the absorbent medium and, in this embodiment, to the bottom of the liquid impermeable foam shell 62. The M-configured pleats are also advantageous in that they provide recovery from lateral compression forces. Foam shell 62 has upper outwardly extending flanges 66 to which are adhered liquid permeable nonwoven facing fabric 64. There are adhesive means on the bottom of the foam shell to facilitate adhering the pad to the wearer's garment. The adhesive means comprise a tape 79 coated on both sides with a pressure sensitive adhesive 60 and are protected prior to use with a removable cover sheet 61 and there may, of course, also be adhesive means (not shown) on the upper or bottom surface of the pad to detachably join it to the rear fecal pad.

The structures shown in FIGS. 6 and 7 are disclosed in greater detail in simultaneously filed U.S. patent application Ser. No. 464,487, the teachings of which are incorporated herein by reference.

Figure 8:
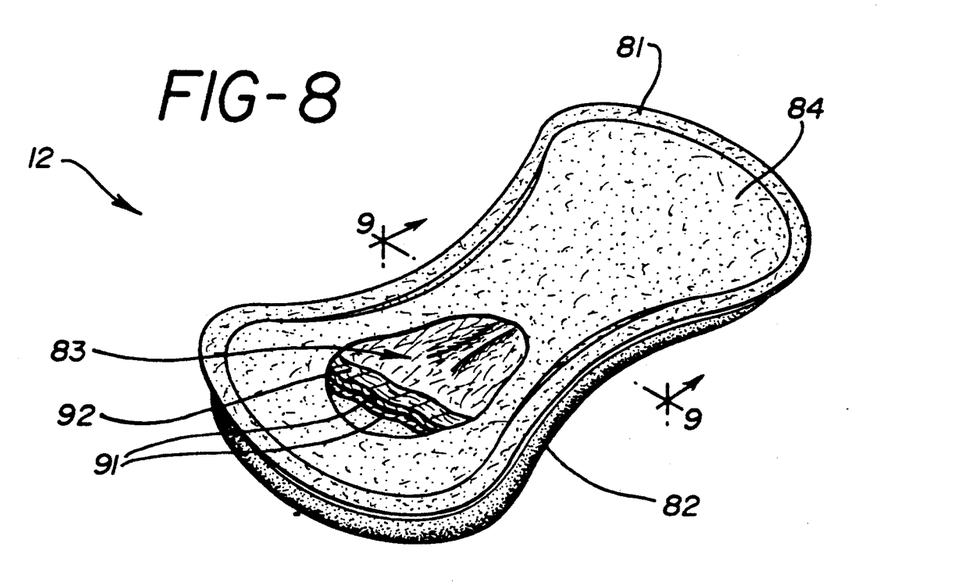
FIG. 8 is a perspective view, also with parts cut away, of another embodiment of a front urinary pad comprising the disposable containment device of this invention.

FIG. 8 illustrates yet another embodiment of a front urinary pad 12 suitable for use in the containment device 10 of this invention. Absorbent core 83 is pleated in an M-configuration, and is inserted into liquid-impermeable shell 82. Liquid-permeable nonwoven facing 84 is adhered to flange 81 of the shell to enclose the absorbent core therein. The absorbent core utilized in this embodiment differs from that of the previously disclosed embodiment, however, in that it utilizes the highly liquid absorptive and retentive properties of peat moss.

Figure 9:
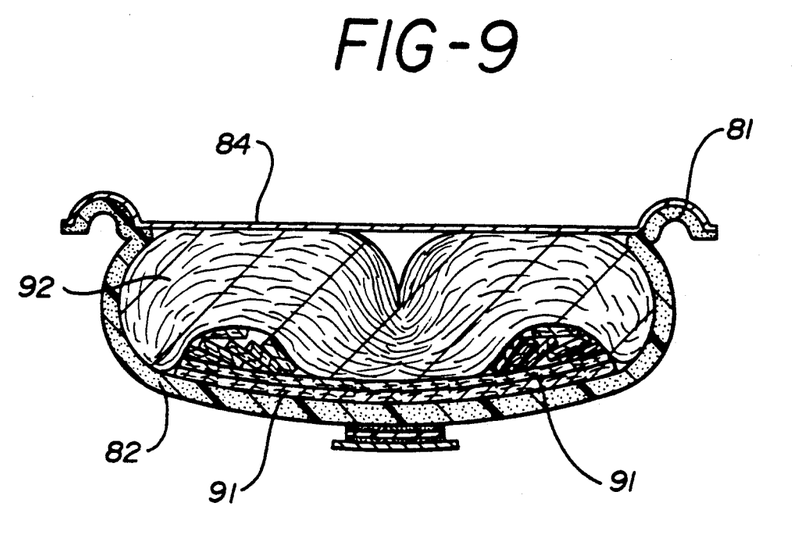
FIG. 9 is a cross-sectional view taken along line 9—9 of FIG. 8.

Absorbent core 83 of the embodiment of FIG. 8 is shown in more detail in the cross-sectional view in FIG. 9. The absorbent core 83 comprises two layers 91,91 of a tenderized peat product, and, on top thereof, facing upwards towards the wearer of the product, is the receiving layer 92. The receiving layer is formed of a material which is capable of absorbing body fluid more rapidly than does the peat moss product, but which does not exhibit the overall liquid absorption and retention properties of the peat moss product 91. The receiving layer therefore operates to "receive" and hold the body fluid until it is absorbed by the layers of peat moss product adjacent to it. Preferably, receiving layer 92 should be capable of absorbing at least about 12 grams of aqueous liquid per gram of receiving layer. The receiving layer comprises a fibrous web of wood pulp fibers and non-cellulosic fibers, e.g., about 50–95 weight percent wood pulp fibers and about 5 to 50 weight percent non-cellulosic synthetic fibers like polyester fibers. A particularly preferred embodiment utilizes as the receiving layer a web of 80% by weight wood pulp and 20% bicomponent (polyester core/polyethylene sheath) fibers having a denier of 3 and a length of 1½ inches. Receiving layer 92 preferably has a basis weight of 11 oz/yd$^2$.

The absorbent core 83, comprising at least one layer of peat moss product 91 and receiving layer 92, is pleated into an M-configuration. The peat moss material comprising the absorbent core can, even after tenderizing, tend to be stiff and lack flexibility. Lengthwise slits 102, shown in FIG. 10, can be provided in the material if enhanced flexibility is desired.

Figure 10:
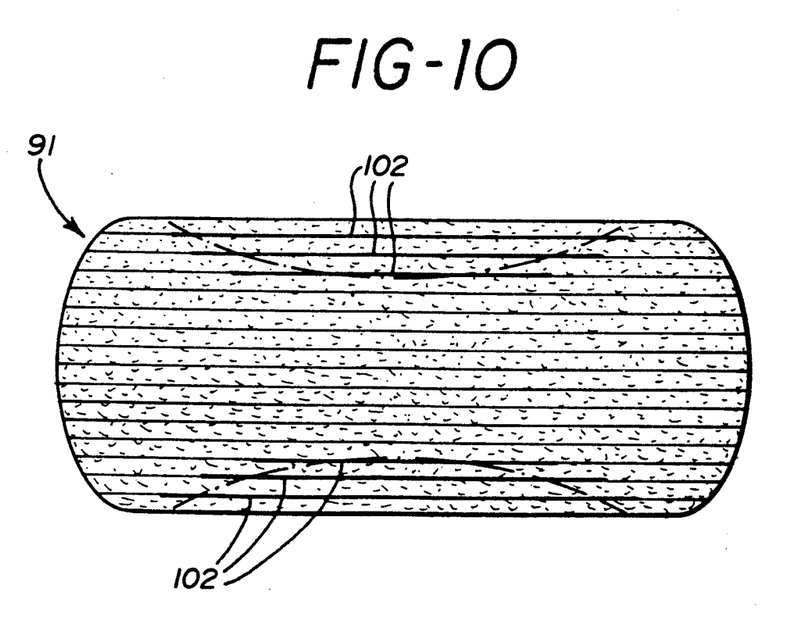
FIG. 10 is a top plan view of an absorbent peat moss element utilized in the pad illustrated in FIGS. 8 and 9.

The structures shown in FIGS. 8, 9 and 10 are described in greater detail in simultaneously filed U.S. patent application Ser. No. 464,493, the teachings of which are incorporated herein by reference.

Figure 11:
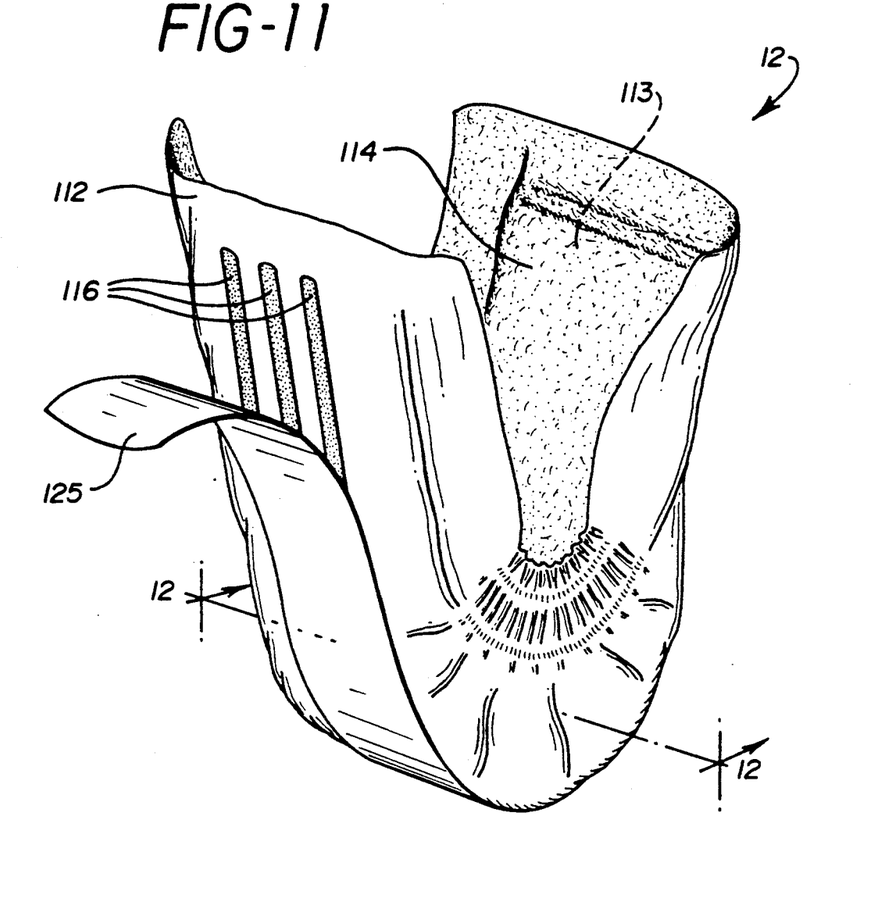
FIG. 11 is a perspective view of yet another embodiment of a front urinary pad comprising the disposable containment device of this invention.

FIG. 11 illustrates another embodiment of a front urinary pad of this invention. In this embodiment, the backing 112 is a sheet of liquid impermeable material, such as a polyolefin film. Absorbent core 113 is sandwiched between the backing 112 and a liquid-permeable facing 114. The three elements, the backing 112, the absorbent core 113 and the facing 114, are combined as shown in the drawings. Elastic means 115 in the crotch area of the product cause the product to have a cup-shaped configuration. There may be adhesive means 116 on the bottom of the backing to facilitate adhering the pad to the wearer's garment. These adhesive means are protected prior to use by removable cover strip 125.

Figure 12:
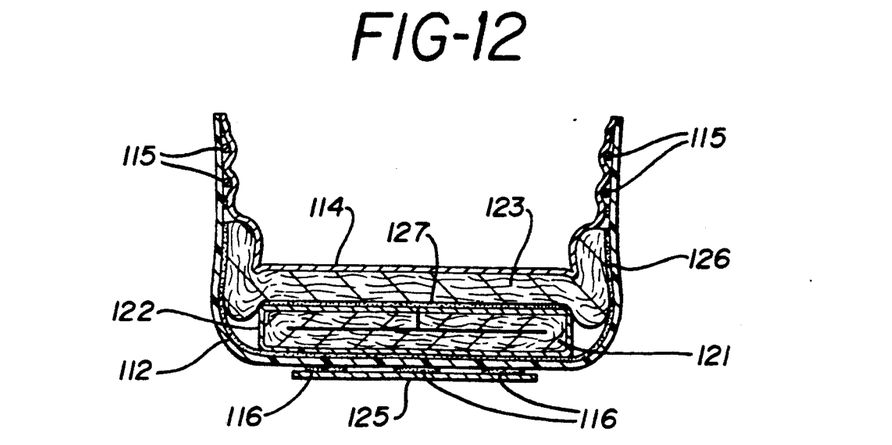
FIG. 12 is a cross-sectional view taken along line 12—12 of FIG. 11.

FIG. 12 is a cross-sectional view of the pad illustrated in FIG. 11. As shown, an absorbent member 121 comprises a sheet of a tenderized peat product folded back on itself in a C-configuration and surrounded by a layer of tissue 122 (e.g., 0.6 oz/yd$^2$ paper). Adjacent to the absorbent member 121, and placed so as to face upwards towards the wearer of the product, is a receiving layer 123, made as described in connection with the previous embodiment. The receiving layer 123 is adhered to the absorbent member 121 with a layer of adhesive 127. The receiving layer 123 is greater in width than the absorbent member 121 and extends partially over the side edges of the absorbent member when the product is in its cup-like configuration. A layer of adhesive 126 adheres both the bottom surface of the absorbent member 121, i.e., that surface facing the garment of the wearer, and the side portions of the receiving layer 123 extending beyond the width of the absorbent member 121, to backing sheet 112. The upper surface of receiving layer 123, i.e. that surface facing the wearer, is kept in contact with liquid permeable facing 114 by frictional engagement of their respective fibrous constituents. Elastic means 115 along the side edges of the pad in the crotch, when contracted, cause the pad to assume its cup-like configuration.

The structures shown in FIGS. 11 and 12 are described in greater detail in simultaneously filed U.S. patent application Ser. No. 464,490, the teachings of which are incorporated herein by reference.

From the foregoing, it will be observed that numerous variations and modifications may be effected without departing from the true spirit and scope of the novel concept of this invention.

What is claimed is:

1. A disposable urinary and fecal waste containment product comprising:
   a separate front urinary pad and a separate rear fecal pad detachably joined together, each of said pads independently comprising a liquid impermeable backing, an absorbent core and a liquid permeable facing;
   said rear fecal pad being substantially square or rectangular and having a top, bottom and two lateral edges;
   said pads being detachably joined together at the bottom edge of said rear fecal pad;
   said rear fecal pad further comprising elastic means along its lateral edges and its top edge so as to cause said pad to be gathered and to assume a bowl-like configuration;
   wherein said front urinary pad further comprises as the liquid-impermeable backing a substantially flexible shell and said shell contains therein as the absorbent core and absorbent core comprising:
   at least one sheet of a tenderized peat moss, said layer being cut adjacent to each lengthwise edge in one or more slits to aid lateral compression folding of the sheet, and
   adjacent to said at least one sheet of tenderized peat moss and disposed upwardly so as to face the wearer of said pad, a receiving layer comprising an absorbent cellulosic material,
   said absorbent core being pleated to form therein a center channel in a lengthwise direction and being inserted into said substantially flexible shell;
   and a liquid-permeable facing adhered to said shell so as to entrap said absorbent unit in said shell.

2. The containment product according to claim 1 wherein, in said absorbent core, said at least one sheet of tenderized peat moss being cut adjacent to each lengthwise edge in a series of lengthwise slits which increase in length from the center of the sheet to aid lateral compression folding of the sheet, and said receiving layer comprises a fibrous web comprising about 70 to 80 weight percent wood pulp and about 20 to 30 weight percent non-cellulosic synthetic fibers; said absorbent core being pleated in a M-configuration to form therein a center channel in a lengthwise direction.

3. A disposable urinary and fecal waste containment product comprising:
   a separate front urinary pad and a separate rear fecal pad detachably joined together, each of said pads independently comprising a liquid impermeable backing, an absorbent core and a liquid permeable facing;
   said rear fecal pad being substantially square or rectangular and having a top, bottom and two lateral edges;
   said pads being detachably joined together at the bottom edge of said rear fecal pad;
   said rear fecal pad further comprising elastic means along its lateral edges and its top edge so as to cause said pad to be gathered and to assume a bowl-like configuration;
   said front urinary pad further comprising as the absorbent core, an absorbent core comprising at least one sheet of tenderized peat moss and, adjacent to said at least one sheet of tenderized peat moss and disposed upwardly so as to face the wearer of the pad, a receiving layer comprising an absorbent cellulosic material, said receiving layer being larger in dimension then said sheet of tenderized peat moss so as to substantially cover said sheet of said tenderized peat moss.

4. The containment product of claim 3 wherein said front urinary pad further comprises the elastic means along the side edges of said pad in the crotch portion thereof so as to cause said pad to be gathered and to assume a cup-like configuration.

5. The containment product of claim 3 wherein said rectangular sheet of tenderized peat moss is folded back upon itself in the C-configuration and wrapped in tissue and wherein said receiving layer comprises a fibrous web comprising about 70 to 85 weight percent wood pulp and about 15 to 30 weight percent polyester core/polyethylene sheath by component fibers.

* * * * *